United States Patent
Fischetti et al.

(12) 
(10) Patent No.: US 6,248,324 B1
(45) Date of Patent: *Jun. 19, 2001

(54) BACTERIAL PHAGE ASSOCIATED LYSING ENZYMES FOR TREATING DERMATOLOGICAL INFECTIONS

(76) Inventors: Vincent Fischetti, 448 Joan Ct., West Hempstead, NY (US) 11552; Lawrence Loomis, 11374 Buckelberry Path, Columbia, MD (US) 21044

( * ) Notice: Subject to any disclaimer, the term of this patent is extended or adjusted under 35 U.S.C. 154(b) by 0 days.

This patent is subject to a terminal disclaimer.

(21) Appl. No.: 09/671,879

(22) Filed: Sep. 28, 2000

Related U.S. Application Data

(63) Continuation of application No. 09/395,636, filed on Sep. 14, 2000, now Pat. No. 6,056,954, which is a continuation-in-part of application No. 09/497,495, filed on Apr. 18, 2000, which is a continuation-in-part of application No. 08/962,523, filed on Oct. 31, 1997, now Pat. No. 5,997,862.

(51) Int. Cl.[7] .................................................. A61K 38/43
(52) U.S. Cl. ........................ 424/94.1; 424/45; 424/450; 424/433; 424/474; 424/430; 424/431; 424/436; 514/2; 514/937
(58) Field of Search ........................ 424/45, 450, 94.1, 424/433, 474, 430, 431, 436; 514/2, 937

(56) References Cited

U.S. PATENT DOCUMENTS

| | | |
|---|---|---|
| 4,062,941 | 12/1977 | Davies . |
| 5,985,271 | 11/1999 | Fischetti et al. . |
| 5,997,862 | 12/1999 | Fischetti et al. . |
| 6,017,528 | 1/2000 | Fischetti et al. . |
| 6,056,954 | 5/2000 | Fischetti et al. . |
| 6,056,955 | 5/2000 | Fischetti et al. . |

*Primary Examiner*—Raj Bawa
(74) *Attorney, Agent, or Firm*—Jonathan E. Grant; Grant Patent Services

(57) ABSTRACT

The present invention discloses a composition for dermatological infections by the use of a lytic enzyme in a carrier suitable for topical application to dermal tissues. The method for the treatment of dermatological infections comprises administering a composition comprising effective amount of a therapeutic agent, with the therapeutic agent comprising a lytic enzyme produced by infecting a bacteria with phage specific for that bacteria.

12 Claims, 1 Drawing Sheet

BACTERIAL PHAGE ASSOCIATED LYSING ENZYMES FOR TREATING DERMATOLOGICAL INFECTIONS

The following application is a continuation-in-part of Ser. No. 09/497,495 filed Apr. 18, 2000 which is a continuation of Ser. No. 09/395,636 filed Sep. 14, 2000, now U.S. Pat. No. 6,056,954 which is a continuation-in-part of U.S. Pat. application Ser. No. 08/962,523, filed Oct. 31, 1997, now U.S. Pat. No. 5,997,862.

DESCRIPTION

BACKGROUND OF THE INVENTION

1. Field of the Invention

The present invention discloses a method and composition for the treatment of bacterial infections by the use of a lysing enzyme blended with an appropriate carrier suitable for the treatment of the infection.

2. Description of the Prior Art

In the past, antibiotics have been used to treat various infections. The work of Selman Waksman in the introduction and production of Streptomycetes, Dr. Fleming's discovery of penicillin, are well known as well as the work of numerous others in the field of antibiotics. Over the years, there have been additions and chemical modifications to the "basic" antibiotics in attempts to make them more powerful, or to treat people allergic to these antibiotics.

Others have found new uses for these antibiotics. U.S. Pat. No. 5,260,292 (Robinson et al.) discloses the topical treatment of acne with aminopenicillins. The method and composition for topically treating acne and acneiform dermal disorders includes applying an amount of an antibiotic selected from the group consisting of ampicillin, amoxicillin, other aminopenicillins, and cephalosporins, and derivatives and analogs thereof, effective to treat the acne and acneiform dermal disorders. U.S. Pat. No. 5,409,917 (Robinson et al.) discloses the topical treatment of acne with cephalosporins.

However, as more antibiotics have been prescribed or used at an ever increasing rate for a variety of illnesses, increasing numbers of bacteria have developed a resistance to antibiotics. Larger doses of stronger antibiotics are now being used to treat ever more resistant strains of bacteria. Multiple antibiotic resistant bacteria have consequently developed. The use of more antibiotics and the number of bacteria showing resistance has led to increasing the amount of time that the antibiotics need to be used. Broad, non-specific antibiotics, some of which have detrimental effects on the patient, are now being used more frequently. Also, antibiotics do not easily penetrate mucus linings. Additionally, the number of people allergic to antibiotics appears to be increasing.

Consequently, other efforts have been sought to first identify and then kill bacteria.

Attempts have been made to treat bacterial diseases with by the use of bacteriophages. U.S. Pat. No. 5,688,501 (Merril, et al.) discloses a method for treating an infectious disease caused by bacteria in an animal with lytic or non-lytic bacteriophages that are specific for particular bacteria.

U.S. Pat. No. 4,957,686 (Norris) discloses a procedure of improved dental hygiene which comprises introducing into the mouth bacteriophages parasitic to bacteria which possess the property of readily adhering to the salivary pellicle.

It is to be noted that the direct introduction of bacteriophages into an animal to prevent or fight diseases has certain drawbacks. Specifically, the bacteria must be in the right growth phase for the phage to attach. Both the bacteria and the and the phage have to be in the correct and synchronized growth cycles. Additionally, there must be the right number of phages to attach to the bacteria; if there are too many or too few phages, there will either be no attachment or no production of the lysing enzyme. The phage must also be active enough. The phages are also inhibited by many things including bacterial debris from the organism it is going to attack. Further complicating the direct use of bacteriophage to treat bacterial infections is the possibility of immunological reactions, rendering the phage non-functional.

Consequently, others have explored the use of other safer and more effective means to treat and prevent bacterial infections.

U.S. Pat. No. 5,604,109 (Fischetti et al.) relates to the rapid detection of Group A streptococci in clinical specimens, through the enzymatic digestion by a semi-purified Group C streptococcal phage associated lysin enzyme. The lytic enzyme of this patent is used in U.S. Pat. No. 5,997,862 (Fischetti, et. al.), U.S. Pat. No. 5,985,271, (Fischetti et al.) and U.S. Pat. No. 6,017,528 (Fischetti et al.) which disclose the use of an oral delivery mode, such as a candy, chewing gum, lozenge, troche, tablet, a powder, an aerosol, a liquid or a liquid spray, containing a lysin enzyme produced by group C streptococcal bacteria infected with a C1 bacteriophage for the prophylactic and therapeutic treatment of Streptococcal A throat infections, commonly known as strep throat.

U.S. Pat. No. 6,056,955 (Fischetti et al.) discloses the topical treatment of streptococcal infections.

SUMMARY OF THE INVENTION

The method for obtaining and purifying the lytic enzyme produced by a bacteria infected with the bacteriophage is known in the art. Some recent evidence suggests that the phage enzyme that lyses the streptococcus organism may actually be a bacterial enzyme that is used to construct the cell wall and the phage. While replicating in the bacterium, a phage gene product may cause the upregulation or derepression of bacterial enzyme for the purpose of releasing the bacteriophage. These bacterial enzymes may be tightly regulated by the bacterial cell and are used by the bacteria for the construction and assembly of the cell wall.

The use of these lytic enzymes for the prophylactic and therapeutic treatment of bacterial diseases, however, has not been explored, except by the inventors of the present invention. Consequently, the present invention discloses the extraction and use of a variety of bacterial phage associated lytic enzymes for the treatment of a wide variety of illnesses caused by bacterial infections.

The use of phage associated lytic enzymes produced by the infection of a bacteria with a bacteria specific phage has numerous advantages for the treatment of diseases. As the phage are targeted for specific bacteria, the lytic enzymes do not interfere with normal flora. Also, lytic phages primarily attack cell wall structures which are not affected by plasmid variation. The actions of the lytic enzymes are fast and do not depend on bacterial growth.

Lytic enzymes can be directed to the mucosal lining, where, in residence, they will be able to kill colonizing bacteria.

It is an object of the invention to use phage associated enzymes to prophylactically and therapeutically treat bacterial diseases.

The invention (which incorporates U.S. Pat. No. 5,604,109 in its entirety by reference) uses an enzyme produced by the bacterial organism after being infected with a particular bacteriophage as either a prophylactic treatment for preventing those who have been exposed to others who have the symptoms of an infection from getting sick, or as a therapeutic treatment for those who have already become ill from the infection. The present invention is based upon the discovery that phage lytic enzymes specific for bacteria infected with a specific phage can effectively and efficiently break down the cell wall of the bacterium in question. At the same time, in most if not all cases, the semipurified enzyme is lacking in mammalian cell receptors and therefore is non-destructive to mammalian proteins and tissues when present during the digestion of the bacterial cell wall. The same general technique used to produce and purify the lysin enzyme in U.S. Pat. No. 5,604,109 may be used to manufacture other lytic enzymes produced by bacteria infected with a bacteriophage specific for that bacteria. Depending on the bacteria, there may be variations in the growth media and conditions.

In one embodiment of the invention, the prophylactic and therapeutic treatment of a variety of illnesses caused by *Streptococcal pneumoniae, Streptococcus fasciae,* and *Hemophilus influenza* are disclosed. In another embodiment of the invention, gram negative bacterial infections caused by Listeria, Salmonella, *E coli,* and Campylobacter, are treated by the use of lytic enzymes. These and other bacteria, which can infect the digestive system, can be treated by incorporating the lytic enzymes in suppository enemas, in syrups, or in other carriers to get directly to the site of the infection(s).

In another embodiment of the invention, lytic enzymes are incorporated into bandages to prevent or treat infections of burns and wounds. In yet another embodiment of the invention, the lytic enzymes of phage associated with Staphylococcus or Pseudomonas are incorporated into bandages to prevent or treat infections of burns and wounds.

Vaginal infections caused by Group B Streptococcus can cause premature birth and subsequent complications resulting in neonatal sepsis. Lysin incorporated into tampons specific for group B strep would prevent infection of the neonate during birth without disturbing normal vaginal flora so that women would not be overcome by yeast infection as a result of antibiotic therapy.

In another embodiment of the invention, eye drops containing lytic enzymes of Hemophilus, Pseudomonas, and/or Staphylococcus can be used to directly treat eye infections. Treatment with lytic enzymes are faster and more expedient than with antibiotics.

In yet another embodiment of the invention the phage associated lytic enzyme is put into a carrier which is placed in an inhaler to treat or prevent the spread of diseases localized in the mucus lining of the oral cavity and lungs. Specific lytic enzymes for tuberculosis have been isolated and can be used.

In another embodiment of the invention the lytic enzyme is administered in the form of a candy, chewing gum, lozenge, troche, tablet, a powder, an aerosol, a liquid, a liquid spray, or toothpaste for the prevention or treatment of bacterial infections associated with upper respiratory tract illnesses.

In another embodiment of the invention, species specific lytic enzymes can be used in the treatment of bacterial infections associated with topical or dermatological infections, administered in the form of a topical ointment or cream. In another embodiment of the invention, the lytic enzyme would be administered in an aqueous form. In yet another embodiment of the invention, lysostaphin, the enzyme which lyses Staphylococcus aureus, can be included in the therapeutic agent. In a further embodiment of the invention, conventional antibiotics may be included in the therapeutic agent with the lytic enzyme, and with or without the presence of lysostaphin. More than one lytic enzyme may also be included in the prophylactic or therapeutic agent.

DETAILED DESCRIPTION OF THE INVENTION

Figure 1:
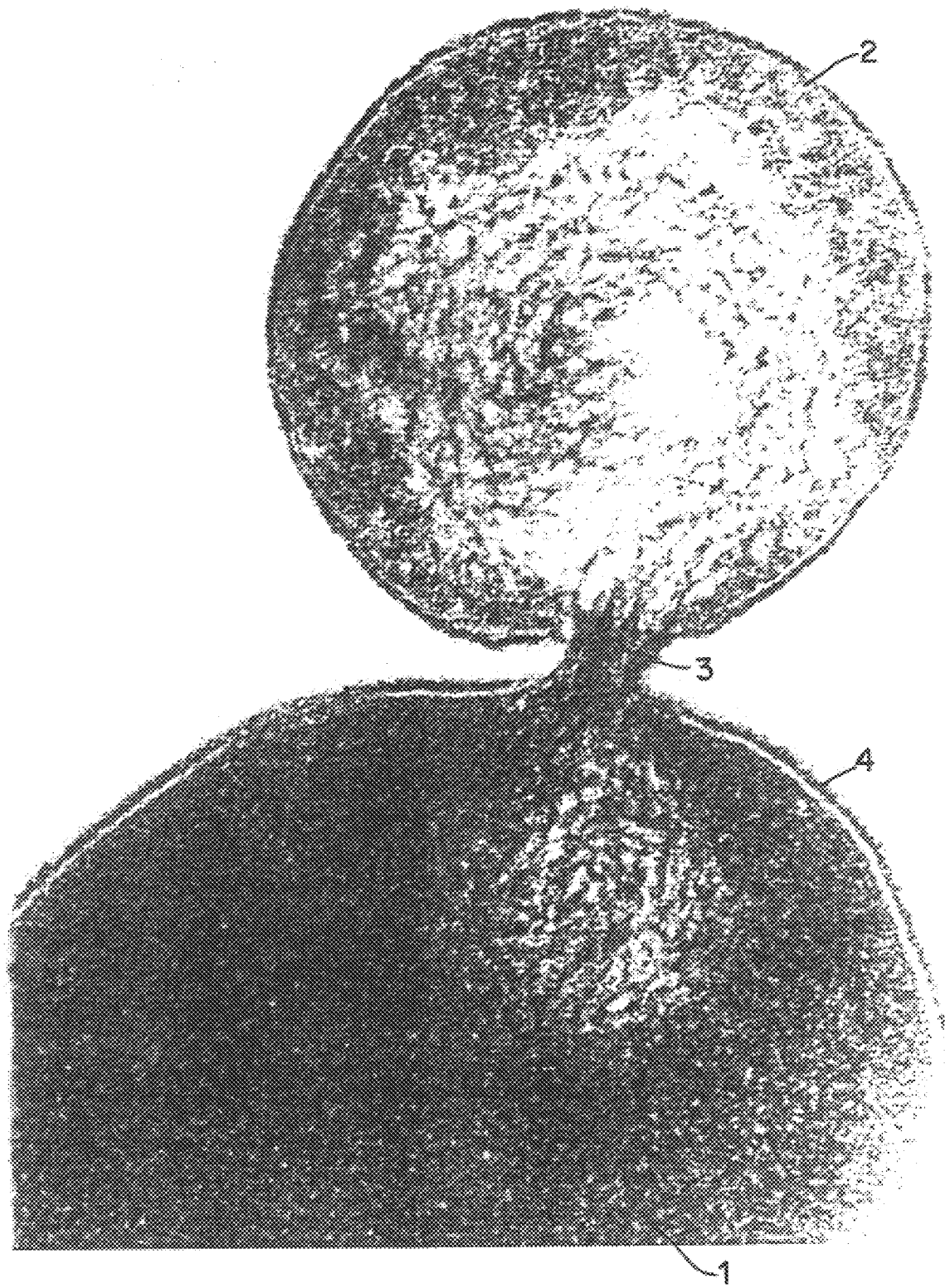
FIG. 1 is an electron micrograph of group A streptococci treated with lysin showing the collapse of the cell wall and the cell contents pouring out.

The method for treating bacterial infections comprises treating the infection with a therapeutic agent comprising an effective amount of at least one lytic enzyme produced by a bacteria infected with a bacteriophage specific for the bacteria. The lytic enzyme is preferably in an environment having a pH which allows for activity of said lytic enzyme.

The lytic enzyme can be used for the treatment or prevention of Hemophilus influenza, Pseudomonas, *Streptococcus pneumoniae, Streptococcus fasciae,* Streptococcus group B, Listeria, Salmonella, *E. coli,* Campylobacter, and other bacteria, and any combination thereof.

For example, if there is a bacterial infection of the upper respiratory tract, the infection can be prophylactically or therapeutically treated with a composition comprising an effective amount of at least one lytic enzyme produced by a bacteria being infected with a bacteriophage specific for that bacteria, and a carrier for delivering the lytic enzyme to a mouth, throat, or nasal passage. It is preferred that the lytic enzyme is in an environment having a pH which allows for activity of the lytic enzyme. If an individual has been exposed to someone with the upper respiratory disorder, the lytic enzyme will reside in the mucosal lining and prevent any colonization of the infecting bacteria.

Two examples of bacteria which infect the upper respiratory system are *Streptococcus pneumoniae* and *Hemophilus influenzae*. In recent years, there has been an increase in the number of people, particularly children and the elderly, that are infected or are carriers of penicillin resistant Streptococcus pneumoniae and Hemophilus. While these bacteria are normally harmless residents of the host, they are opportunistic organisms that are able to cause infections when the resistance of the host has been compromised. By eliminating or reducing the number of these organisms in the upper respiratory tract, there will be a commensurate reduction in the number of infections by these bacteria.

Infection of the Hemophilus bacteria by Bacteriophage HP1 (a member of the P2-like phage family with strong similarities to coliphages P2 and 186, and some similarity to the retronphage Ec67) produces a lytic enzyme capable of lysing the bacteria. The lytic enzyme for *Streptococcus pneumoniae,* previously identified as an N-acetylmuramoyl-L-alanine amidase, is produced by the infecting *Streptococcus pneumoniae* with the Pal bacteriophage. The therapeutic agent can contain either or both of the lytic enzymes produced by these two bacteria, and may contain other lytic enzymes for other bacteria. The composition which may be used for the prophylactic and therapeutic treatment of a strep infection includes the lysin enzyme and a means of application (such as a carrier system or an oral delivery mode) to reach the mucosal lining of the oral and nasal cavity, such that the enzyme is put in the carrier system or oral delivery mode to reach the mucosa lining. Another infection which can be treated prophylactically is Streptococcus group A, which can produce what is commonly known as "strep" throat. When group C Streptococci are infected with a C1 bacteriophage, a lysin enzyme is produced specific for the lysing of Streptococcus group A.

Prior to, or at the time the lysin enzyme is put in the carrier system or oral delivery mode, it is preferred that the enzyme be in a stabilizing buffer environment for maintaining a pH range between about 4.0 and about 9.0, more preferably between about 5.5 and about 7.5 and most preferably at about 6.1.

The stabilizing buffer should allow for the optimum activity of the lysin enzyme. The buffer may be a reducing reagent, such as dithiothreitol. The stabilizing buffer may also be or include a metal chelating reagent, such as ethylenediaminetetracetic acid disodium salt, or it may also contain a phosphate or citrate-phosphate buffer.

Means of application include, but are not limited to direct, indirect, carrier and special means or any combination of means. Direct application of the lytic enzyme may be by nasal sprays, nasal drops, nasal ointments, nasal washes, nasal injections, nasal packings, bronchial sprays and inhalers, or indirectly through use of throat lozenges, or through use of mouthwashes or gargles, or through the use of ointments applied to the nasal nares, the bridge of the nose, or the face or any combination of these and similar methods of application. The forms in which the lysin enzyme maybe administered include but are not limited to lozenges, troches, candies, injectants, chewing gums, tablets, powders, sprays, liquids, ointments, and aerosols.

The lozenge, tablet, or gum into which the lytic enzyme is added may contain sugar, corn syrup, a variety of dyes, non-sugar sweeteners, flavorings, any binders, or combinations thereof. Similarly, any gum based products may contain acacia, carnauba wax, citric acid, corn starch, food colorings, flavorings, non-sugar sweeteners, gelatin, glucose, glycerin, gum base, shellac, sodium saccharin, sugar, water, white wax, cellulose, other binders, and combinations thereof.

Lozenges may further contain sucrose, corn starch, acacia, gum tragacanth, anethole, linseed, oleoresin, mineral oil, and cellulose, other binders, and combinations thereof. In another embodiment of the invention, sugar substitutes are used in place of dextrose, sucrose, or other sugars.

The enzyme may also be placed in a nasal spray, wherein the nasal spray is the carrier. The nasal spray can be a long acting or timed release spray, and can be manufactured by means well known in the art. An inhalant may also be used, so that the phage enzyme may reach further down into the bronchial tract, including into the lungs.

Any of the carriers for the lytic enzyme may be manufactured by conventional means. However, it is preferred that any mouthwash or similar type products not contain alcohol to prevent denaturing of the enzyme. Similarly, when the lytic enzyme is being placed in a cough drop, gum, candy or lozenge during the manufacturing process, such placement should be made prior to the hardening of the lozenge or candy but after the cough drop or candy has cooled somewhat, to avoid heat denaturation of the enzyme.

The enzyme may be added to these substances in a liquid form or in a lyophilized state, whereupon it will be solubilized when it meets body fluids such as saliva. The enzyme may also be in a micelle or liposome.

The effective dosage rates or amounts of the lytic enzyme to treat the infection will depend in part on whether the lytic will be used therapeutically or prophylactically, the duration of exposure of the recipient to the infectious bacteria, the size and weight of the individual, etc. The duration for use of the composition containing the enzyme also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of enzyme believed to provide for an effective amount or dosage of enzyme may be in the range of about 100 units/ml to about 100,000 units/ml of fluid in the wet or damp environment of the nasal and oral passages, and possibly in the range of about 100 units/ml to about 10,000 units/ml. More specifically, time exposure to the active enzyme units may influence the desired concentration of active enzyme units per ml. It should be noted that carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depends on the nature of infection, whether treatment is to be prophylactic or therapeutic, and other variables.

While this treatment may be used in any mammalian species, the preferred use of this product is for a human.

This composition and method may also be used for the treatment of Streptococcus A infections of the respiratory tract. When using this composition for a Streptococcus A infection, the lysin phage enzyme should be used for the prophylactic prevention of Streptococcus infections. Similarly, in another embodiment of the invention, this method may be used for the therapeutic and, preferably, the prophylactic treatment of tuberculosis. In a preferred embodiment of the invention, the phage associated lysing enzyme for *Mycobacteria tuberculosis* is placed in a carrier in an inhaler. The carrier may be sterile water or a water base, or any other carrier used in an inhaler for dispersing drugs into the bronchial tract. The phage associated lytic enzyme specific for tuberculosis is subject to the same conditions as the phage associated lytic enzyme for other lytic enzymes. Specifically, prior to, or at the time the enzyme is put in the carrier system or oral delivery mode, it is preferred that the enzyme be in a stabilizing buffer environment for maintaining a pH range between about 4.0 and about 9.0.

The stabilizing buffer should allow for the optimum activity of the lytic enzyme. The buffer may be a reducing reagent, such as dithiothreitol. The stabilizing buffer may also be or include a metal chelating reagent, such as ethylenediaminetetracetic acid disodium salt, or it may also contain a phosphate or citrate-phosphate buffer.

For the prophylactic and therapeutic treatment of tuberculosis, the phage associated lytic enzyme associated with tuberculosis may also be applied by direct, indirect, carriers and special means or any combination of means. Direct application of the lytic enzyme may be by nasal sprays, nasal drops, nasal ointments, nasal washes, nasal injections, nasal packings, bronchial sprays and inhalers, or indirectly through use of throat lozenges, or through use of mouthwashes or gargles, or through the use of ointments applied to the nasal nares, the bridge of the nose, or the face or any combination of these and similar methods of application. The forms in which the lytic enzyme may be administered include but are not limited to lozenges, troches, candies, injectants, chewing gums, tablets, powders, sprays, liquids, ointments, and aerosols. For the therapeutic treatment of tuberculosis, the bronchial sprays and aerosols are most beneficial, as these carriers, or means of distributing the composition, allow the lytic enzyme to reach the bronchial tubes and the lungs. An appropriate transport carrier may be attached to the enzyme to transport the enzyme across the cell membrane to the site of the bacteria.

The lozenge, tablet, or gum into which the lytic enzyme is added may contain sugar, corn syrup, a variety of dyes, non-sugar sweeteners, flavorings, any binders, or combinations thereof. Similarly, any gum based products may contain acacia, carnauba wax, citric acid, corn starch, food colorings, flavorings, non-sugar sweeteners, gelatin, glucose, glycerin, gum base, shellac, sodium saccharin, sugar, water, white wax, cellulose, other binders, and combinations thereof.

Lozenges may further contain sucrose, corn starch, acacia, gum tragacanth, anethole, linseed, oleoresin, mineral oil, and cellulose, other binders, and combinations thereof. In another embodiment of the invention, sugar substitutes are used in place of dextrose, sucrose, or other sugars. However, to tackle bacterial infections in the lung, the use of an inhaler carrier the lytic enzyme in a carrier is preferred.

Another use of a lytic enzyme is for the treatment of bacterial infections of the digestive tract. The method for treating a bacterial infection of the digestive tract comprises treating the bacterial infection with composition comprising an effective amount of at least one lytic enzyme produced by a bacteria infected with a bacteriophage specific for the bacteria, and a carrier for delivering said lytic enzyme to the digestive tract. In a preferred embodiment of the invention, the bacterial infections being treated are being caused by gram negative bacteria selected from the group consisting of Listeria, Salmonella, *E. coli,* and Campylobacter. However, this method and composition will effectively treat other bacteria, when the appropriate lytic enzyme is used.

In a preferred embodiment of the invention, the carrier is selected from the group consisting of suppository enemas, syrups, or enteric coated pills. These proposed carriers can be made by conventional methods. However, the only difference in their manufacture is that the enzyme being placed in the carrier must not be allowed to denature. To that end, the enzyme should be incorporated into a carrier which does not contain alcohol, and which has been cooled to a temperature that will not cause the denaturing of the enzyme. The enzyme may be incorporated in a lyophilized state, or maybe incorporated in a liposome before being placed in the suppository, syrup or enteric coated pill. The enzyme placed in the composition or carrier should be in an environment having a pH which allows for activity of the lytic enzyme. To this end, the pH of the composition is preferably kept in a range of between about 2 and about 11, more preferably in a range of between about between about 4.0 and about 9.0, and even more preferably at a pH range of between about 5.5 and about 7.5. As described above with the other lytic enzyme, the pH can be moderated by the use of a buffer. The buffer may contain a reducing agent, and more specifically dithiothreitol. The buffer may also be a a metal chelating reagent, such as ethylenediaminetetracetic disodium salt or the buffer may contain a citrate-phosphate buffer. As with all compositions described in this patent, the composition may, further include a bactericidal or bacteriostatic agent as a preservative.

The lytic enzyme is preferably present in a concentration of about 100 to about 500,000 active enzyme units per milliliter of fluid in the wet environment of the gastrointestinal tract, preferably about 100 to about 100,000 active enzyme units per milliliter of fluid, and preferably present in a concentration of about 100 to about 10,000 active enzyme units per milliliter of fluid in the wet environment of the gastrointestinal tract.

The suppository is known in the art, and is made of glycerin, fatty acids, and similar type substances that dissolve at body temperature. As the suppository dissolves, the phage associated lytic enzyme will be released.

Another composition and use of the lytic enzyme is for the therapeutic or prophylactic treatment of bacterial infections of burns and wounds of the skin. The composition comprises an effective amount of at least one lytic enzyme produced by a bacteria infected with a bacteriophage specific for the bacteria and a carrier for delivering at least one lytic enzyme to the wounded skin. The mode of application for the lytic enzyme includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes but is not limited to a smear, spray, a time-release patch, a liquid absorbed wipe, and combinations thereof. The lytic enzyme may be applied to a bandage either directly or in one of the other carriers. The bandages may be sold damp or dry, wherein the enzyme is in a lyophilized form on the bandage. This method of application is most effective for the treatment of burns.

The carriers of the compositions of the present invention may comprise semi-solid and gel-like vehicles that include a polymer thickener, water, preservatives, active surfactants or emulsifiers, antioxidants, sun screens, and a solvent or mixed solvent system. U.S. Pat. No. 5,863,560 (Osborne) discusses a number of different carrier combinations which can aid in the exposure of the skin to a medicament.

Polymer thickeners that may be used include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL.RTM." (B. F. Goodrich, Cleveland, Ohio), "HYPAN.RTM." (Kingston Technologies, Dayton, N.J.), "NATROSOL.RTM." (Aqualon, Wilmington, Del.), "KLUCEL.RTM." (Aqualon, Wilmington, Del.), or "STABILEZE.RTM." (ISP Technologies, Wayne, N.J.). Preferably, the gelling agent comprises between about 0.2% to about 4% by weight of the composition. More particularly, the preferred compositional weight percent range for "CARBOPOL.RTM." is between about 0.5% to about 2%, while the preferred weight percent range for "NATROSOL.RTM." and "KLUCEL.RTM." is between about 0.5% to about 4%. The preferred compositional weight percent range for both "HYPAN.RTM." and "STABILEZE.RTM." is between about 0.5% to about 4%.

"CARBOPOL.RTM." is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL.RTM." is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

Preservatives may also be used in this invention and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Titanium dioxide may be used as a sunscreen to serve as prophylaxis against photosensitization. Alternative sun screens include methyl cinnamate. Moreover, BHA may be used as an antioxidant, as well as to protect ethoxydiglycol and/or dapsone from discoloration due to oxidation. An alternate antioxidant is BHT.

Pharmaceuticals for use in all embodiments of the invention include antimicrobial agents, anti-inflammatory agents, antiviral agents, local anesthetic agents, corticosteroids, destructive therapy agents, antifungals, and antiandrogens. In the treatment of acne, active pharmaceuticals that may be used include antimicrobial agents, especially those having anti-inflammatory properties such as dapsone, erythromycin, minocycline, tetracycline, clindamycin, and other antimicrobials. The preferred weight percentages for the antimicrobials are 0.5% to 10%.

Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. A preferred concentration for local anesthetics is about 0.025% to 5% by weight of the total composition. Anesthetics such as benzocaine may also be used at a preferred concentration of about 2% to 25% by weight.

Corticosteroids that may be used include betamethasone dipropionate, fluocinolone actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide are recommended at concentrations of about 0.01% to 1.0% by weight. Preferred concentrations for corticosteroids such as hydrocortisone or methylprednisolone acetate are from about 0.2% to about 5.0% by weight.

Destructive therapy agents such as salicylic acid or lactic acid may also be used. A concentration of about 2% to about 40% by weight is preferred. Cantharidin is preferably utilized in a concentration of about 5% to about 30% by weight. Typical antifungals that may be used in this invention and their preferred weight concentrations include: oxiconazole nitrate (0.1% to 5.0%), ciclopirox olamine (0.1% to 5.0%), ketoconazole (0.1% to 5.0%), miconazole nitrate (0.1% to 5.0%), and butoconazole nitrate (0.1% to 5.0%). For the topical treatment of seborrheic dermatitis, hirsutism, acne, and alopecia, the active pharmaceutical may include an antiandrogen such as flutamide or finasteride in preferred weight percentages of about 0.5% to 10%.

Typically, treatments using a combination of drugs include antibiotics in combination with local anesthetics such as polymycin B sulfate and neomycin sulfate in combination with tetracaine for topical antibiotic gels to provide prophylaxis against infection and relief of pain. Another example is the use of minoxidil in combination with a corticosteroid such as betamethasone diproprionate for the treatment of alopecia ereata. The combination of an anti-inflammatory such as cortisone with an antifungal such as ketoconazole for the treatment of tinea infections is also an example.

In one embodiment, the invention comprises a dermatological composition having about 0.5% to 10% carbomer and about 0.5% to 10% of a pharmaceutical that exists in both a dissolved state and a micro particulate state. The dissolved pharmaceutical has the capacity to cross the stratum corneum, whereas the micro particulate pharmaceutical does not. Addition of an amine base, potassium, hydroxide solution, or sodium hydroxide solution completes the formation of the gel. More particularly, the pharmaceutical may include dapsone, an antimicrobial agent having anti-inflammatory properties. A preferred ratio of micro particulate to dissolved dapsone is five or less.

In another embodiment, the invention comprises about 1% carbomer, about 80–90% water, about 10% ethoxydiglycol, about 0.2% methylparaben, about 0.3% to 3.0% dapsone including both micro particulate dapsone and dissolved dapsone, and about 2% caustic material. More particularly, the carbomer may include "CARBOPOL.RTM. 980" and the caustic material may include sodium hydroxide solution.

In a preferred embodiment, the composition comprises dapsone and ethoxydiglycol, which allows for an optimized ratio of micro particulate drug to dissolved drug. This ratio determines the amount of drug delivered, compared to the amount of drug retained in or above the stratum corneum to function in the supracorneum domain. The system of dapsone and ethoxydiglycol may include purified water combined with "CARBOPOL.RTM." gelling polymer, methylparaben, propylparaben, titanium dioxide, BHA, and a caustic material to neutralize the "CARBOPOL.RTM."

Any of the carriers for the lytic enzyme may be manufactured by conventional means. However, if alcohol is used in the carrier, the enzyme should be in a micelle, liposome, or a "reverse" liposome, to prevent denaturing of the enzyme. Similarly, when the lytic enzyme is being placed in the carrier, and the carrier is, or has been heated, such placement should be made after the carrier has cooled somewhat, to avoid heat denaturation of the enzyme. In a preferred embodiment of the invention, the carrier is sterile.

The enzyme may be added to these substances in a liquid form or in a lyophilized state, whereupon it will be solubilized when it meets a liquid body.

The effective dosage rates or amounts of the lytic enzyme to treat the infection, and the duration of treatment will depend in part on the seriousness of the infection, the duration of exposure of the recipient to the infectious bacteria, the number of square centimeters of skin or tissue which are infected, the depth of the infection, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzyme believed to provide for an effective amount or dosage of enzyme may be in the range of about 100 units/ml to about 500,000 units/ml of composition, preferably in the range of about 1000 units/ml to about 100,000 units/m/l, and most preferably from about 10,000 to 100,000 units/ml. The amount of active units per ml and the duration of time of exposure depends on the nature of infection, and the amount of contact the carrier allows the lytic enzyme to have. It is to be remembered that the enzyme works best when in a fluid environment. Hence, effectiveness of the enzyme is in part related to the amount of moisture trapped by the carrier. In another preferred embodiment, a mild surfactant in an amount effective to potentiate the therapeutic effect of the lytic enzyme. Suitable mild surfactants include, inter alia, esters of polyoxyethylene sorbitan and fatty acids (Tween series), octylphenoxy polyethoxy ethanol (Triton-X series), n-Octyl-.beta.-D-glucopyranoside, n-Octyl-.beta.-D-thioglucopyranoside, n-Decyl-.beta.-D-glucopyranoside, n-Dodecyl-.beta.-D-glucopyranoside, and biologically occurring surfactants, e.g., fatty acids, glycerides, monoglycerides, deoxycholate and esters of deoxycholate.

In order to accelerate treatment of the infection, the therapeutic agent may further include at least one complementary agent which can also potentiate the bactericidal activity of the lytic enzyme. The complementary agent can be penicillin, synthetic penicillins bacitracin, methicillin, cephalosporin, polymyxin, cefaclor. Cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceflizoxime, ceftriaxone, cefriaxone moxalactam , cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef. mafate, chelating agents and any combinations thereof in amounts which are effective to synergistically enhance the therapeutic effect of the lytic enzyme.

Additionally, the therapeutic agent may further comprise the enzyme lysostaphin for the treatment of any *Staphylococcus aureus* bacteria. Mucolytic peptides, such as lysostaphin, have been suggested to be efficacious in the treatment of *S. aureus* infections of humans (Schaffner et al., Yale J. Biol. & Med., 39:230 (1967) and bovine mastitis caused by *S. aureus* (Sears et al., J. Dairy Science, 71 (Suppl. 1): 244(1988)). Lysostaphin, a gene product of *Staphylococcus simulans*, exerts a bacteriostatic and bactericidal effect upon *S. aureus* by enzymatically degrading the polyglycine crosslinks of the cell wall (Browder et al., Res. Comm., 19: 393–400 (1965)). U.S. Pat. No. 3,278,378 describes fermentation methods for producing lysostaphin from culture media of *S. staphylolyticus,* later renamed *S. simulans.* Other methods for producing lysostaphin are further described in U.S. Pat. Nos. 3,398,056 and 3,594,284. The gene for lysostaphin has subsequently been cloned and sequenced (Recsei et al., Proc. Natl. Acad. Sci. USA, 84: 1127–1131 (1987)). The recombinant mucolytic bactericidal protein, such as r-lysostaphin, can potentially circumvent problems associated with current antibiotic therapy because of its targeted specificity, low toxicity and possible reduction of biologically active residues. Furthermore, lysostaphin is also active against non-dividing cells, while most antibiotics require actively dividing cells to mediate their effects (Dixon et al., Yale J. Biology and Medicine, 41: 62–68 (1968)). Lysostaphin, in combination with the lysin enzyme, can be used in the presence or absence of the listed antibiotics. There is a degree of added importance in using both lysostaphin and the lysin enzyme in the same therapeutic agent. Frequently, when a body has a bacterial infection, the infection by one genus of bacteria weakens the body or changes the bacterial flora of the body, allowing other potentially pathogenic bacteria to infect the body. One of the bacteria that sometimes co-infects a body is *Staphylococcus aureus*. Many strains of *Staphylococcus aureus* produce penicillinase, such that Staphylococcus, Streptococcus, and other gram positive bacterial strains will not be killed by standard antibiotics. Consequently, the use of the lysin and lysostaphin, possibly in combination with antibiotics, can serve as the most rapid and effective treatment of bacterial infections. In yet another preferred embodiment, the invention may include mutanolysin, and lysozyme In preferred embodiments of the invention, the lytic enzymes for Pseudomonas, Staphylococcus, and Streptococcus, jointly or individually, may be incorporated into the carrier, or into a bandage to be used on burn patients, or in a solution or cream carrier.

Yet another use of lytic enzymes is for the prophylactic or therapeutic treatment of vaginal infections. This treatment comprises treating the vaginal infection with an effective amount of at least one lytic enzyme produced by a bacteria being infected with a bacteriophage specific for that bacteria, wherein that lytic enzyme is incorporated in a carrier to be placed in a vagina. The preferred carrier is a tampon, or vaginal douche. A pad may also be used as a carrier, although it is not as effective. While any number of bacteria could be treated using this composition and method, it is believed that the most optimum use of this treatment composition and method would be for the treatment of an *E. coli* and Streptococcus B infection. Vaginal infections caused by Group B Streptococcus can cause neonatal meningitis resulting in brain damage and premature death. Lytic enzyme incorporated into tampon specific for group B Strep would eliminate the group B organisms without disturbing normal flora so that woman would not be overcome by yeast infection post antibiotic therapy. The use of the lytic enzyme in the vagina would best provide a prophylactic effect, although therapeutic use would also be advisable.

To produce a pad or tampon containing the enzyme, the lytic enzyme can be applied in a solution to the tampon, and allowed to dry. The lytic enzyme may be incorporated into the pad or tampon by any other means known in the art, including lyophilization, spraying, etc. The tampons and pads may also be kept slightly moist, and in a sealed wrapper until ready for use. In that case, bactericide and bacteriostatic compounds and inhibitors should be present in the tampons and pads. The method to be used for incorporating the lytic enzyme into the tampon or pad can be one of the methods known in the art for incorporating a pharmaceutical product. In another embodiment of the invention, the lytic enzyme is incorporated into a vaginal suppository. The vaginal suppository into which the lytic enzyme is being incorporated may be a standard vaginal suppository, comprised of glyceride, alginate, starch, other standard binders and any combinations thereof.

When using a tampon as the carrier, it is best to insert the tampon in the vagina and leave it in for up to 12 hours to distribute the enzyme vaginally.

As with other lytic enzymes, it is preferable that the pH be kept in a range of about 4.0 and about 9.0 even more preferably at a pH range of between about 5.5 and about 7.5. As described above with the other lytic enzyme, the pH can be moderated by the use of a buffer. The buffer may contain a reducing agent, and more specifically dithiothreitol. The buffer may also contain a metal chelating reagent, such as ethylenediaminetetracetic disodium salt or the buffer may be a citrate-phosphate buffer. As with all compositions described in this patent, the composition may, further include a bactericidal or bacteriostatic agent as a preservative.

The lytic enzyme is preferably present in a concentration of about 100 to about 500,000 active enzyme units per milliliter of fluid in the wet environment of the vaginal tract, preferably about 100 to about 100,000 active enzyme units per milliliter of fluid, and preferably present in a concentration of about 100 to about 10,000 active enzyme units per milliliter of fluid in the wet environment of the vaginal tract.

Another use of the invention is for the prophylactic and therapeutic treatment of eye infections. The method of treatment comprises administering eye drops which comprise an effective amount of at least one lytic enzyme produced by the bacteria being infected with a bacteriophage specific for the bacteria and a carrier capable of being safely applied to an eye, with the carrier containing the lytic enzyme. In a preferred embodiment of the invention, the bacteria being treated is Hemophilus or Staphylococcus The eye drops are in the form of an isotonic solution. The pH of the solution should be adjusted so that there is no irritation of the eye, which in turn would lead to possibly infection by other organisms, and possibly to damage to the eye. While the pH range should be in the same range as for other lytic enzymes, the most optimal pH will be in the range of from 6.0 to 7.5. Similarly, buffers of the sort described above for the other lytic enzymes should also be used. Other antibiotics which are suitable for use in eye drops may be added to the composition containing the lytic enzymes. Bactericides and bacteriostatic compounds may also be added.

It is to be remembered that all of the enzymes can be used for prophylactic and therapeutic treatments of the bacteria for which the enzymes are specific.

It is also to be remembered that a carrier may have more than one lytic enzyme. For instance, A throat lozenge may comprise just a lysin enzyme (which lyses the Streptococcus A strain causing "strep" throat, or it may also include the lytic enzymes for Hemophilus. Similarly, the carrier for treating burns and wounds, or infections of the skin, may contain just one lytic enzyme, or a combination of lytic enzymes, for the treatment of Pseudomonas, Streptococcus, Staphylococcus, or any other of a number of bacteria.

Lytic enzymes can also be used to fight dental caries. Specifically, a lytic enzyme specific for *Streptococcus mutans* may be incorporated in a toothpaste or oral wash. Similarly, this lytic enzyme may also be incorporated into a chewing gum or lozenge. Any other carrier can be used that allows for the exposure of the mouth, gums, and teeth to the lytic enzyme.

The lytic enzyme may also be incorporated in a lyophilized or dried form in tooth powder. If the lytic enzyme is to be used in an oral wash, it is preferred that the oral wash not contain any alcohol, so as to not denature the enzyme. The enzyme can also be in a liposome when mixed in with the toothpaste or oral wash. The concentrations of the enzyme units per ml of toothpaste or mouth wash can be in the range of from about 100 units/ml to about 500,000 units/ml of composition, preferably in the range of about 1000 units/ml to about 100,000 units/ml, and most preferably from about 10,000 to 100,000 units/ml. The pH of the toothpaste or oral wash should be in a range that allows for the optimum performance of the enzyme, while not causing any discomfort to the user of the toothpaste or oral wash.

The following example illustrates the isolation of the lytic enzyme.

Phage Associated Enzyme

The group C phage lysin enzyme is prepared as follows:

Group C streptococcal strain 26RP66 (ATCC #21597) or any other group C streptococcal strain is grown in Todd Hewitt medium at 37.degree. C. to an OD of 0.23 at 650 nm in an 18 mm tube. Group C bacteriophage (C1) (ATCC #21597-B1) at a titer of 5.times. 10.sup.6 is added at a ratio of 1 part phage to 4 parts cells. The mixture is allowed to remain at 37.degree. C. for 18 min at which time the infected cells are poured over ice cubes to reduce the temperature of the solution to below 15.degree. C. The infected cells are then harvested in a refrigerated centrifuge and suspended in 1/300th of the original volume in 0.1M phosphate buffer, pH 6.1 containing 5.times.10.sup.-3 M dithiothreitol and 10 ug of DNAase. The cells will lyse releasing phage and the lysin enzyme. After centrifugation at 100,000.times. g for 5 hrs to remove most of the cell debris and phage, the enzyme solution is aliquoted and tested for its ability to lyse Group A Streptococci.

The number of units/ml in a lot of enzyme is determined to be the reciprocal of the highest dilution of enzyme required to reduce the OD650 of a suspension of group A streptococci at an OD of 0.3 to 0.15 in 15 minutes. In a typical preparation of enzyme 4.times.10.sup.5 to 4.times.10.sup.6 units are produced in a single 12 liter batch.

The enzyme may be diluted in a stabilizing buffer containing the appropriate conditions for stability, maximum enzymatic activity, inhibitors of nonspecific reactions, and in some configurations contains specific antibodies to the Group A carbohydrate. The preferred embodiment is to use a lyophilized reagent which can be reconstituted with water. The stabilizing buffer can comprise a reducing reagent, which can be dithiothreitol in a concentration from 0.001M to 1.0M, preferably 0.005M. The stabilizing buffer can comprise an immunoglobulin or immunoglobulin fragments in a concentration of 0.001 percent to 10 percent, preferably 0.1 percent. The stabilizing buffer can comprise a citrate-phosphate buffer in a concentration from 0.001M to 1.0M, preferably 0.05M. The stabilizing buffer can have a pH value in the range from 5.0 to 9.0. The stabilizing buffer can comprise a bactericidal or bacteriostatic reagent as a preservative. Such preservative can be sodium azide in a concentration from 0.001 percent to 0.1 percent, preferably 0.02 percent.

The preparation of phage stocks for lysin production is the same procedure described above for the infection of phage and group C streptococcus in the preparation of the lysin enzyme. However, instead of pouring the infected cells over ice, the incubation at 37.degree. C. is continued for a total of 1 hour to allow lysis and release of the phage and also enzyme in the total volume. In order for the phage to be used for subsequent lysin production the residual enzyme must be inactivated or removed to prevent lysis from without of the group C cells rather than phage infection.

The thin section electron micrograph of FIG. 1 shows the results of a group A streptococci 1 treated for 15 seconds with lysin. The micrograph (25,000X magnification) shows the cell contents 2 pouring out through a hole 3 created in the cell wall 4 by the lysin enzyme.

This general technique can be used to produce other lytic enzymes for the treatment of various bacterial infections.

Many modifications and variations of the present invention are possible in light of the above teachings. It is, therefore, to be understood within the scope of the appended claims the invention may be protected otherwise than as specifically described.

What we claim is:

1. A method for treating dermatological bacterial infections comprising:

topically applying to an infected area of skin a therapeutic agent, said therapeutic agent comprising:

an effective amount of at least one lytic enzyme produced by a bacteria infected with a bacteriophage specific for said bacteria wherein said at least one lytic enzyme will lyse at least one said bacteria infecting said skin; and a pharmaceutically acceptable topical carrier for delivering said at least one enzyme to said infected area of said skin.

2. The method according to claim 1, wherein said carrier is selected from the group consisting of an aqueous liquid, an alcohol base, a water soluble gel, a lotion, an ointment, a nonaqueous liquid base, a mineral oil base, a blend of mineral oil and petrolatum, lanolin, liposomes, hydrophilic gelling agents, cross-linked acrylic acid polymers (carbomer), cellulose polymers, hydroxy ethyl cellulose, cellulose gum, MVE/MA decadiene crosspolymers, PVM/MA copolymers, and combinations thereof.

3. The method according to claim 1, wherein the form in which the therapeutic agent is delivered is selected from the group consisting of a spray, a smear, a time release patch, a liquid absorbed wipe, and any combinations thereof.

4. The method according to claim 1, wherein the at least one lytic enzyme is in an environment having a pH which allows for activity of said at least one lytic enzyme.

5. The method according to claim 4, wherein said therapeutic agent further comprises a buffer that maintains pH of the therapeutic agent at a range between about 4.0 to about 9.0.

6. The method according to claim 5, wherein said buffer maintains the pH of the therapeutic agent at the range of between about 5.5 and about 7.5.

7. The method according to claim 5, wherein said buffer comprises a reducing agent.

8. The method according to claim 7, wherein said reducing agent is dithiothreitol.

9. The method according to claim 1, wherein said therapeutic agent further comprises a mild surfactant in an amount effective to potentiate effects of the at least one lytic enzyme.

10. The method according to claim 1, wherein the therapeutic agent further comprises at least one complementary agent which potentiates the bactericidal activity of the at least one lytic enzyme, said complementary agent selected from the group consisting of penicillin, synthetic penicillins bacitracin, methicillin, cephalosporin, polymyxin, cefaclor, Cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroxime axetil, dihydratecephalothin, moxalactam, loracarbef. mafate and chelating agents in an amount effective to synergistically enhance effects of the lytic enzyme.

11. The method according to claim 1, wherein the therapeutic agent further comprises lysostaphin for the treatment of *Staphylococcus aureus*.

12. The method according to claim 1, wherein said at least one lytic enzyme is present in an amount ranging from about 100 to about 500,000 units per milliliter.

* * * * *

UNITED STATES PATENT AND TRADEMARK OFFICE
CERTIFICATE OF CORRECTION

| | |
|---|---|
| PATENT NO. | : 6,248,324 B1 |
| APPLICATION NO. | : 09/671879 |
| DATED | : June 19, 2001 |
| INVENTOR(S) | : Vincent Fischetti and Lawrence Loomis |

It is certified that error appears in the above-identified patent and that said Letters Patent is hereby corrected as shown below:

On the front cover, item (63), please delete

"The following application is a continuation-in-part of Ser. No. 09/497,495 filed April 18, 2000, which is a continuation of Serial No. 09/395,636 filed Sept. 14, 1999, now U.S. Pat. No. 6,058,954 which is a continuation-in-par of U.S. Pat. application Serial No. 08/962,523, filed Oct. 31, 1997, now U.S. Pat No. 5,997,862"

and replace with

--The following application is a continuation-in-part of Ser. No. 09/497,495 filed April 18, 2000, which is a continuation of Serial No. 09/395,636 filed Sept 14, [1999] 2000, now U.S. Pat No. 6,056,954 which is a continuation-in-par of U.S. Pat. application Serial No. 08/962,523, flied Oct. 31, 1997, now U.S. Pat. No. 5,997,862--

Signed and Sealed this

Fifth Day of June, 2007

JON W. DUDAS
*Director of the United States Patent and Trademark Office*